(12) United States Patent
Kumar

(10) Patent No.: US 9,707,069 B2
(45) Date of Patent: Jul. 18, 2017

(54) SUTURE MESH AND METHOD OF USE

(71) Applicant: Avinash Kumar, Lakewood Ranch, FL (US)

(72) Inventor: Avinash Kumar, Lakewood Ranch, FL (US)

(*) Notice: Subject to any disclaimer, the term of this patent is extended or adjusted under 35 U.S.C. 154(b) by 638 days.

(21) Appl. No.: 13/776,083

(22) Filed: Feb. 25, 2013

(65) Prior Publication Data

US 2013/0226204 A1 Aug. 29, 2013

Related U.S. Application Data

(63) Continuation of application No. PCT/US2012/026605, filed on Feb. 24, 2012.

(60) Provisional application No. 61/446,540, filed on Feb. 25, 2011.

(51) Int. Cl.
| | | |
|---|---|---|
| *A61B 17/08* | (2006.01) | |
| *A61F 2/00* | (2006.01) | |
| *A61B 17/04* | (2006.01) | |
| *A61F 2/08* | (2006.01) | |
| *A61B 17/06* | (2006.01) | |

(52) U.S. Cl.
CPC ........ *A61F 2/0063* (2013.01); *A61B 17/0487* (2013.01); *A61F 2/08* (2013.01); *A61F 2/0811* (2013.01); *A61B 2017/06052* (2013.01); *A61B 2017/06176* (2013.01); *A61F 2002/0852* (2013.01)

(58) Field of Classification Search
CPC .................................................. A61F 2/0063
USPC ............... 606/151; 600/37; 623/23.72, 23.74
See application file for complete search history.

(56) References Cited

U.S. PATENT DOCUMENTS

| | | | |
|---|---|---|---|
| 4,941,466 A | 7/1990 | Romano | |
| 5,088,147 A | 2/1992 | MacMillan | |
| 5,268,001 A | 12/1993 | Nicholson et al. | |
| 5,366,480 A | 11/1994 | Corriveau et al. | |
| 5,413,585 A | 5/1995 | Pagedas | |
| 5,486,197 A * | 1/1996 | Le et al. ................ | 606/232 |
| 5,500,000 A * | 3/1996 | Feagin et al. .......... | 606/232 |
| 5,725,529 A | 3/1998 | Nicholson et al. | |
| 5,741,301 A | 4/1998 | Pagedas | |

(Continued)

FOREIGN PATENT DOCUMENTS

| | | |
|---|---|---|
| EP | 0440371 B1 | 12/1996 |
| EP | 0895745 B1 | 8/2003 |

(Continued)

OTHER PUBLICATIONS

Biomet Sports Medicine, Sleeve and Button Soft Tissue Devices, 8 pages.

(Continued)

*Primary Examiner* — Tuan V Nguyen
(74) *Attorney, Agent, or Firm* — Dinsmore & Shohl LLP

(57) ABSTRACT

A medical device comprises a mesh and suture combination, the suture having retaining mechanisms such as beads, balls, ratchet surfaces, oblate spheres and/or disks extending along at least a portion of the length of the suture. A clip or tab may be combined with the retaining mechanisms to fix the suture in place, such as during reconstructive surgery. For example, the mesh and suture combination may be used to fix tendons in place with respect to bones as a bone anchor and/or as a support mesh for repair of torn tendons.

11 Claims, 15 Drawing Sheets

(56) References Cited

U.S. PATENT DOCUMENTS

| | | |
|---|---|---|
| 5,860,978 A | 1/1999 | McDevitt et al. |
| 6,302,886 B1 | 10/2001 | McDevitt et al. |
| 6,416,517 B2 | 7/2002 | Harder et al. |
| 6,830,572 B2 | 12/2004 | McDevitt et al. |
| 6,923,811 B1 | 8/2005 | Carl et al. |
| 6,991,643 B2 | 1/2006 | Saadat |
| 7,081,119 B2 | 7/2006 | Stihl |
| 7,186,262 B2 | 3/2007 | Saadat |
| 7,217,284 B2 | 5/2007 | Houser et al. |
| 7,604,636 B1 | 10/2009 | Walters et al. |
| 7,651,495 B2 | 1/2010 | McDevitt et al. |
| 7,731,721 B2 | 6/2010 | Rathbun et al. |
| 7,771,441 B2 | 8/2010 | Cerundolo |
| 2008/0188936 A1 | 8/2008 | Ball et al. |
| 2009/0198107 A1 | 8/2009 | Park et al. |
| 2009/0228021 A1* | 9/2009 | Leung ............... 606/139 |
| 2010/0069926 A1 | 3/2010 | Goble et al. |
| 2010/0100128 A1 | 4/2010 | McDevitt et al. |
| 2010/0191247 A1 | 7/2010 | Schneider |
| 2010/0191248 A1 | 7/2010 | Mehta et al. |
| 2011/0071548 A1* | 3/2011 | Yeh et al. ............... 606/144 |

FOREIGN PATENT DOCUMENTS

| | | |
|---|---|---|
| EP | 2206482 A1 | 7/2010 |
| WO | 2008097901 A1 | 8/2008 |
| WO | 2009107121 A2 | 9/2009 |

OTHER PUBLICATIONS

Tomier, ArthroTunneler, 7 pages.
Biomet Sports Medicine, 510(K) Summary, 6 pages.
George Sikora, Native Shoulder & Elbow Concepts, Sep. 9, 2009, 6 pages.
Biomet Sports Medicine, Sleeve with ZipLoop(trademark) Fixation Devices, 5 pages.

* cited by examiner

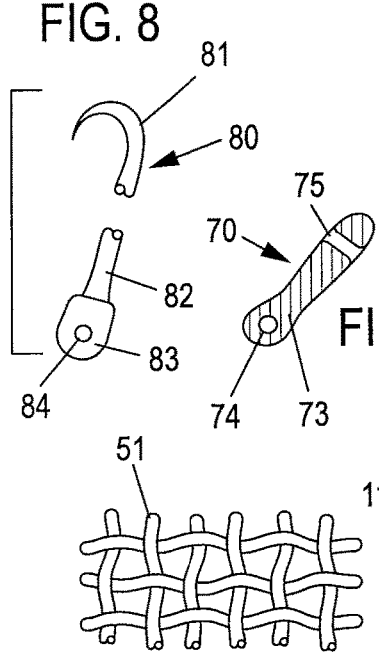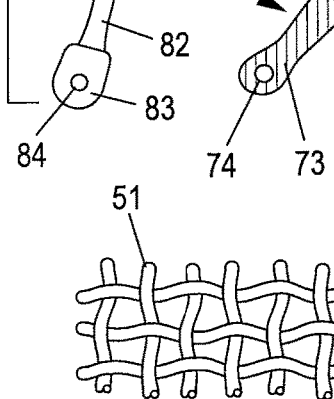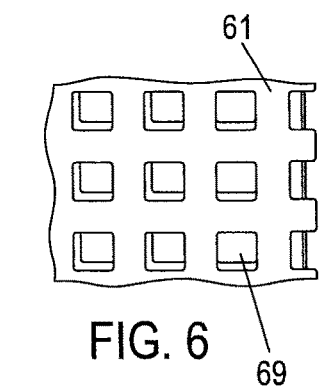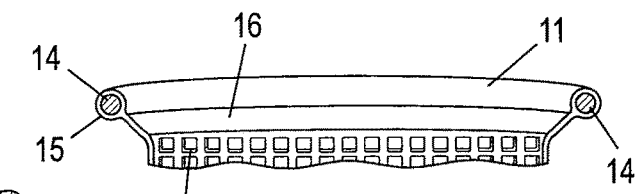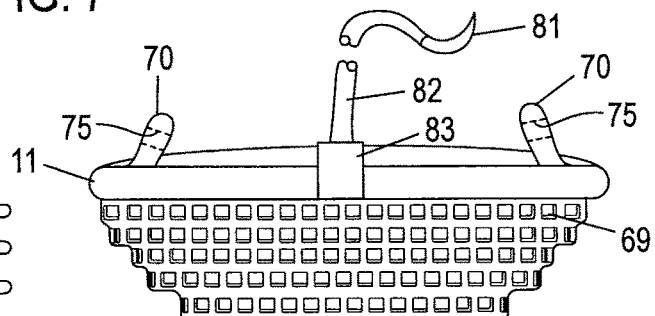

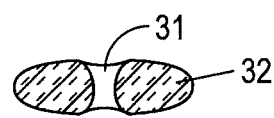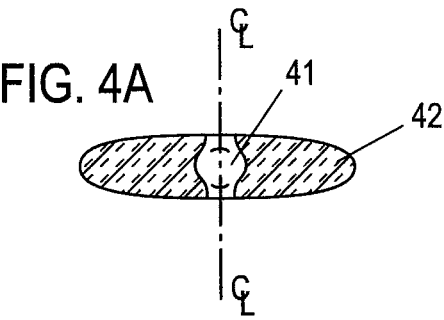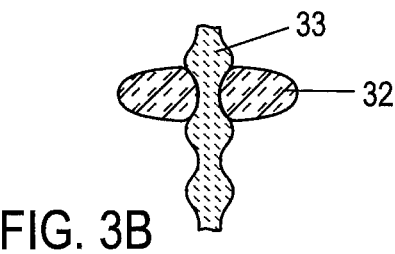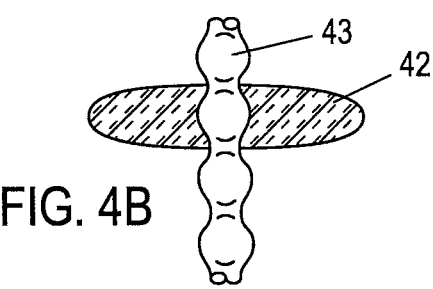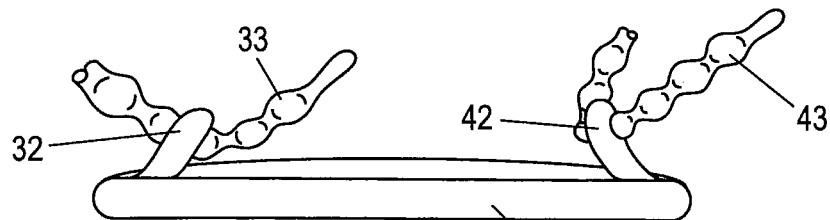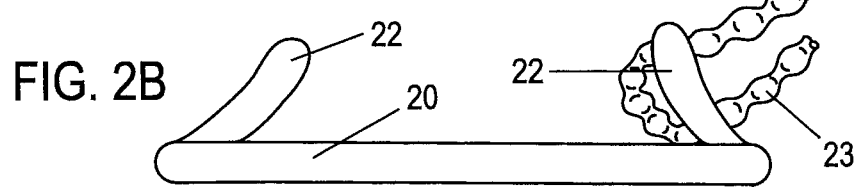

SUTURE MESH AND METHOD OF USE

RELATED APPLICATION

This application is a continuation of PCT/US2012/026605 filed Feb. 24, 2012 which claims priority to U.S. Provisional Application No. 61/446,540 filed on Feb. 25, 2011 and are incorporated by reference herein in their entirety.

FIELD OF THE INVENTION

The field relates to affixing sutures using a transosseous tunnel.

BACKGROUND

Surgical procedures and devices are known for creating transosseous tunnels for attachment of soft tissues, such as tendon and ligaments to bone. Both artificial and natural materials are attached to these soft tissues to repair them, and surgical procedures may move soft tissues from one location to another to repair a damaged, torn or severed tendons or ligaments.

U.S. Pat. Pub. 2008/0188936 and WO 2008/097901 disclose details of rotator cuff repair. The human shoulder is a complex system of hard and soft tissues that exhibits extraordinary mobility using coordinated activation of a variety of muscles, simultaneously. A conventional arthroscopic repair of a torn supraspinatus tendon is disclosed in the background of the publication, reporting that 20-60% of rotator cuff repairs fail. The publication discloses the dilemma with surgery of this type. Any artificial addition to the tissues that takes up too much stress on living tissues can lead to atrophy of the living tissues. In order to heal properly, living tissues must be exposed to a certain level of stress that is within a nominal range for healing. These ranges are known in the art, but devices and techniques that provide optimal healing are not available. Bioabsorbable materials are disclosed both in the background and as an embodiment of the publication's invention. The publication teaches away from making tension members from non-absorbable materials; however, the absorbable materials of the patch and tension members may be reinforced by non-absorbable materials, such as by including non-absorbable fibers in a patch material or tension members, and may be attached by bone anchors. The publication teaches providing coatings on its medical devices, providing biologically active agents for improving healing, for example.

U.S. Pat. No. 5,268,001 discloses a bone fastener for fixing either a suture or a rivet within a predrilled bone hole. The background of this issued patent summarizes the variety of materials and types of bone anchors historically available for using in anchoring soft tissues to bones, either as a rivet or as a suture anchor. The patent discloses a hand held means 70, in FIGS. 3.1 and 3.2 of the patent, which is useful in setting an anchor within an annular portion, fixing the anchor and annular portion within a pre-drilled hole in a bone.

U.S. Pat. No. 7,651,495 discloses a method and apparatus for preventing migration of sutures through transosseous tunnels. Its improved method for attaching soft tissues to bone passes a suture through a transosseous tunnel and uses the suture to affix the soft tissue to the bone. The improved apparatus is an eyelet, which is placed into an end of the bone opposite of the soft tissue and through which the suture passes. The eyelet may be threaded, interference fit or pressure fit using a two piece insertion/expandable member, with the expandable member anchoring the insertion member within the pre-drilled hole through the bone. The patent discloses in its background that it is known that transosseous tunnels are the gold standard of rotator cuff repair, but migration of sutures through the bone itself is a significant complication, particularly in older patients. The patent discloses a known attachment mechanism using plate-like augmentation to reinforce the bone, teaches significant disadvantages of this technique and teaches the advantages of its eyelet approach to preventing migration of the suture through degradation under the force of the sutures on the bone. U.S. Pat. No. 5,725,529 discloses another bone fastener having similar characteristics to other disclosed bone fasteners.

U.S. Pat. Pub. 2010/0191248 discloses an arthroscopic tunnel guide for rotator cuff repair. Its tunnel guide provides a transosseous tunnel having a fixed, non-zero radius of curvature using a bone cutting instrument. This disclosure provides a tool and drill guide that provides a curvature to a transosseous tunnel drilled arthroscopically, allowing arthroscopic surgeons use of a portion of the humeral head that was previously only available by open surgery.

U.S. Pat. Pub. 2010/0191247 discloses another apparatus for drilling a transosseous tunnel. The reference teaches that the drill bit tip acts as an anchor at the far cortex distal from the surface of the humeral head adjacent to the soft tissues, when the anchor is detached from the drill bit, at the distal end of the transosseous tunnel formed by the drill bit tip. The applicant believes that there is a concern with the use of this device in the way described in the publication, which introduces a risk of possible axillary nerve injury during the described procedure, which drills to the inferior-medial aspect of the humeral head.

All of the listed patents and publications in this background are incorporated by reference in their entirety herein for the purposes of providing background and materials selection for biocompatible materials. None of the listed patents provide for a time-saving method to prevent the migration of sutures through transosseous tunnels, while repairing damaged tissues and promoting healing.

SUMMARY

Herein, a suture or sutures is defined as any linear material, traditionally cat gut, silk, polymer thread, metal wire or combinations thereof, that is used to stitch or secure together tissues, whether or not permanent or bioabsorbable, unless otherwise indicated.

A suture mesh may comprise a tape or a net and may be combined with a suture having raised portion along at least a portion of the length of the suture. The raised portions may take the form of a bead, ball, ratchet surface, oblong spheroid and/or disk, for example. In one example, a transosseous suture net comprises, on a retention end, a retainer and, on an opposite end of the net, one or more sutures extending from the net. The opposite end and/or body of the net may be sized in diameter and length to extend entirely through a transosseous tunnel such that the suture or sutures extending from the opposite end extend from a portion of the net outside of the transosseous tunnel. Alternatively, one or more sutures may extend from a suture net and may include the raised portions on a portion of the suture that extends through the transosseous tunnel, preventing or reducing suture migration by keeping the sutures from cutting, abrading or pulling through surrounding bone, and the suture net may extend over a portion of the bone preventing or reducing cutting, abrading or pulling through of the suture net through the underlying bone material. The net and suture materials may be made of a variety of biocompatible materials that are known in the art, such as a high density polyethylene. The net may be made of a sheet and may have holes formed or punched in the sheet or may be a weave or mat. In one example, the interstitial holes in the net are sized to encourage bone in-growth, and the net acts as a scaffold structure for the formation of living tissues, aiding in the healing process. For example, the net may include one or more agents intended to improve healing or in-growth of living tissue, such as disclosed in the references disclosed in the background section. A mesh tape may comprise a mesh having sutures extending from one or both ends of the tape and/or may provide anchors or attachment points for attaching one or more sutures to mesh. A mesh may be dimensioned and used as a suture net or may be used as a reinforcing mesh for a tendon or the like. A retention clip may be combined with a suture having raised portions, such that the clip may be secured on one of the raised portions and fixing the raised portions in relation to tissues of a patient, a mesh or a net, for example.

Notably, the net and mesh are not a plug or anchor. Instead, both are pliable or flexible materials. The net, mesh or a suture extending from the net or mesh may be inserted through a transosseous tunnel, such as by using an insertion device, a probe or a snare. Also, a net or mesh may be used as a support for a tendon or other patient tissues during the process of healing and/or thereafter. An insertion device may have a handle, as disclosed in the references cited in the background section. Alternatively, a tool may not be necessary. A tool may be used merely to push the net or mesh or a suture through the transosseous tunnel or a snare may be used to pull a net or mesh or suture through the transosseous tunnel.

Other combinations and variations of the features disclosed herein may be recognized as within the scope and breadth of the disclosed inventions, which are not limited to the specific examples provided. Advantages of the features disclosed are surprising and unexpected and include reduced time for surgical repairs and improved outcomes compared to known products and procedures.

BRIEF DESCRIPTION OF THE DRAWINGS

FIG. 1A illustrates a retention end of one example of a transosseous suture net.

FIG. 1B illustrates a detail view and partial cross section of a portion of the retention end of FIG. 1A.

FIG. 2A illustrates an example of the use of sutures in one example of a suture end in combination with features of a retention end.

FIG. 2B illustrates another example of the use of sutures in one example of a suture end in combination with an alternative feature of a retention end.

FIG. 3A illustrates an example of a cross section of the features shown in FIGS. 2A and 2B, for example.

FIG. 3B illustrates an example of a suture engaging the feature illustrated in FIG. 3A.

FIG. 4A illustrates another example of a cross section of the features shown in FIGS. 2A and 2B, for example.

FIG. 4B illustrates an example of a suture engaging the feature illustrated in FIG. 4A.

FIG. 5 illustrates a detail view of a woven structure that may be used for the body in one example of a net.

FIG. 6 illustrates a detail view of a non-woven structure that may be used for the body in another example of a net.

FIG. 7 illustrates an example of a retention feature that is retainable on a retainer.

FIG. 8 illustrates an example of a suture feature that is retainable on a retainer.

DETAILED DESCRIPTION

This detailed description provides examples that should not be interpreted as limiting the scope and breadth of the appended claims. The features of these examples may be combined and arranged as recited in the claims, notwithstanding the particular examples provided.

FIG. 1A illustrates a retention end of one example of a transosseous suture net. Such a net may be used to prevent the suture net from pulling through the transosseous channel drilled into a bone, for example. The net 61 may be comprised of a woven fabric, such as the fabric illustrated in FIG. 5, which shows a fabric 51 comprises of strands, which may be a solid or spun strands, for example. Alternatively, the mesh 61 may be comprised of a material having holes 69, which may be formed as part of the process of fabrication of the mesh, such as by a die injection, hot forming, forging, machining, stamping, etching or other processes that result in a continuous material with a two-dimensional grid of openings or holes 69 in the mesh 61, as illustrated in FIG. 6, for example. In the example in FIG. 1A, the mesh 61 is a seamless tubular mesh. In an alternative embodiment, the mesh 61 may be formed as a tape or sheet, for example.

Figure 1C:
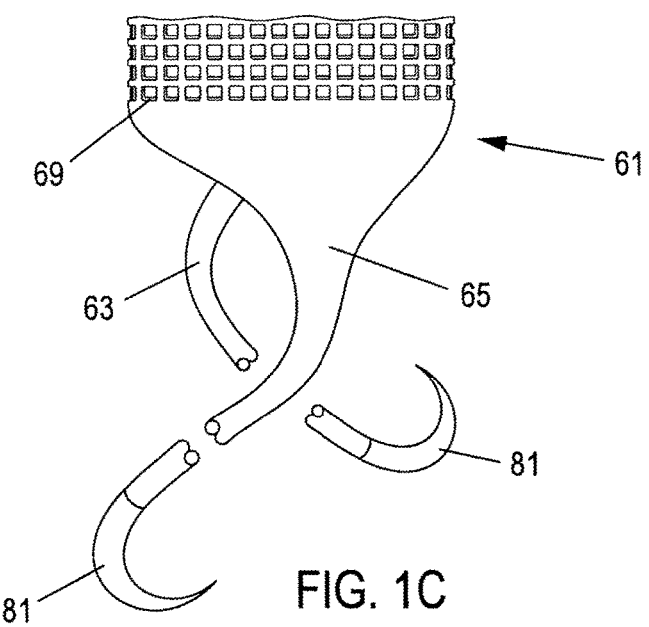
FIG. 1C illustrates an example of a suture end of a transosseous suture net, disposed at an opposite end of the net from the retention end illustrated in FIGS. 1A and 1B, for example.
Figure 1D:
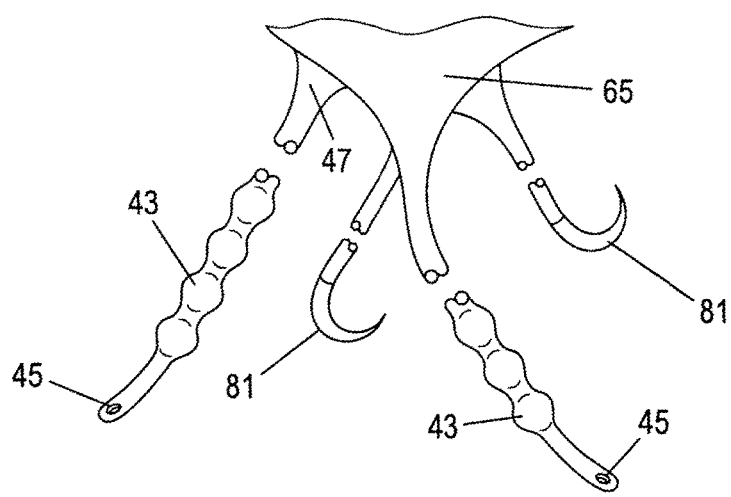
FIG. 1D illustrates another example of a suture end.
Figure 9:
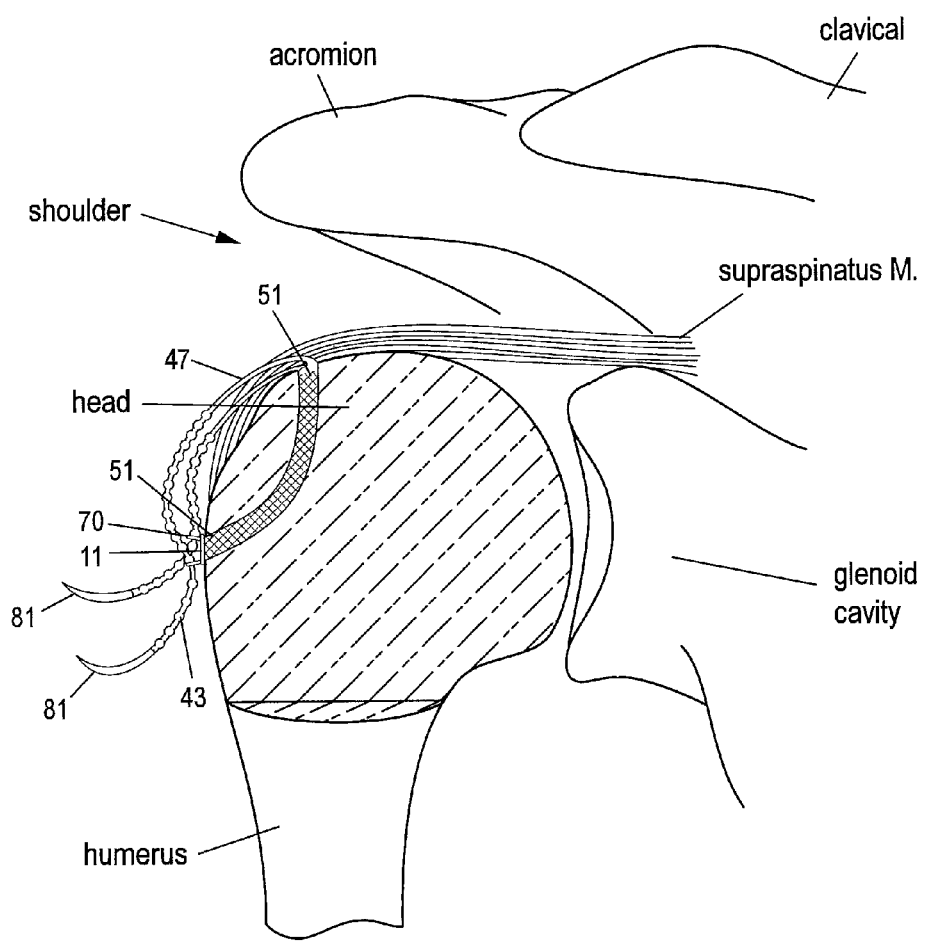
FIG. 9 illustrates an example of a transosseous suture net being used to repair damage to a tendon or ligament in an exemplary method.

FIG. 1B illustrates a detail view and partial cross section of a portion of the retention end of FIG. 1A, for example. In this example, the retention end 11 comprises a portion of the mesh 61, which does not comprise holes 69, that is wrapped and fused about a retention ring 14, which may be made of a metal, a more rigid polymer, a ceramic or another material that tends to prevent the retention end 11 from being drawn through a transosseous channel drilled through a bone. FIG. 9 illustrates use of such a device with the retention end 11 being used to place the end of a transosseus suture net fabric 51 at a surface of a patient's bone. Several attachment points 70, 82 are illustrated in FIG. 1A, such as a tab 70 having a fastening hole 75 or holes or an attached suture 80 with a retention end 82 and a suture end 81 having an optionally integrated suture needle, for example. The tabs 70 or sutures 82 may be attached to the retention end 11, such as by a retention mechanism 73, 83 having a hole 74, 84 through which the retention ring 14 passes, as illustrated in the detailed views of FIGS. 7 and 8, for example. FIG. 1C illustrates an example of a suture end 81 on an opposite end of a transosseous suture net 61, for example. This suture end 81 may be inserted through a transosseous tunnel from either end of the tunnel and may be used for fixing tissues to a patient's bone, for example. For example, a suture 63 incorporating a suture end 81 may be integrally formed with and/or from a material of the mesh 61 as illustrated in FIG. 1C. In the example of FIG. 1D, examples of suture ends 81, 45 are illustrated, one having a suture needle 81 and the other having a hole 45 formed in the end. The suture 63 may have raised portions 43 formed along the length of the suture 63, which allows the suture to be adjustably retained, for example.

Figure 1F:
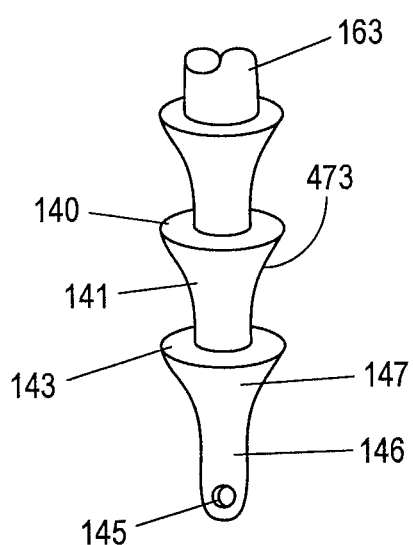
FIG. 1F illustrates a detail view of another example of a portion of a suture extending from a suture end, providing a ratcheted surface.
Figure 1E:
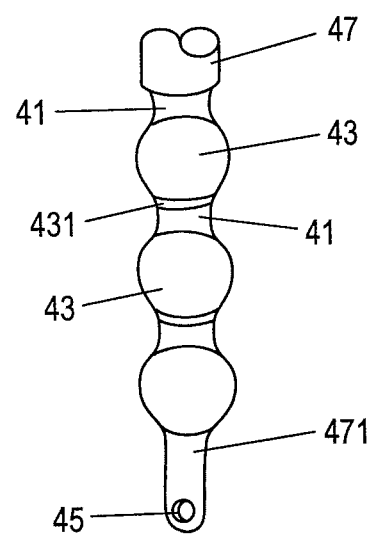
FIG. 1E illustrates a detail view of an example of a portion of a suture extending from a suture end, presenting a suture with retention balls made of a material that is crosslinkable in situ.
Figure 1G:
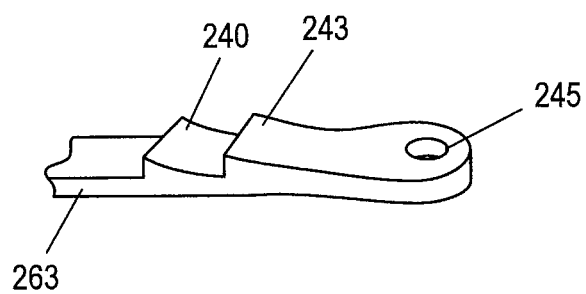
FIG. 1G illustrates a detail view of yet another example of a suture end providing a ratcheted surface.

FIGS. 1E-1F illustrate alternative examples of an end portion of a suture 473, 263, 471, presenting a suture with an adjustable ratchet mechanism as part of a suture. In FIG. 1E, retention balls 43 are connected by ligands 41 to each other and to a suture 47, 471, and the retention balls 43 may be made of a material that is crosslinkable in situ with a retention tab 70, for example. FIG. 1F illustrates a detail view of another example of a portion of a suture extending from a suture end, providing a ratchet surface 140 extending from a suture 163 and a tapered surface 141 preferably for a one-way ratcheting mechanism that resists or prevents a suture from pulling back through a retention tab 70 or a hole in a tissue, for example, while allowing the suture to pull through the tab 70 in order to tighten the suture and/or to fix a tissue in place. FIG. 1G illustrates an alternative ratchet mechanism the presents a flat form factor with a raised portion 240 and a tapered portion 243 extending between a slot, slit or hole 245 and a tape-like suture 263. Any number or length of raised portions may be provided at or before and end of a suture to allow for adjustable retention of the suture in a tab or tissue, for example.

FIG. 2A illustrates an example of a monolithic retention end 20 and the use of sutures in one example of a suture end 33, 43 in combination with features of the retention end 20, such as tabs 32, 42. FIG. 2B illustrates an alternative example of the use of sutures in one example of a suture end 23 in combination with an alternative feature of a retention end, having a pair of holes in each tab 22. FIGS. 3A and 3B illustrate an example of a cross section of a tab 32 and a suture 33 as illustrated in FIGS. 2A and 2B, while FIGS. 4A and 4B illustrate an alternative example of a suture tab 42 engaging a ball in a suture 43, which may be made of a polymer crosslinkable with the material of the tab 42, for example, such as using a chemical reaction or an ultraviolet reaction to initiate or increase the rate of a crosslinking reaction, for example.

FIG. 9 illustrates an example of a transosseous suture net being used to repair damage to a tendon or ligament in an exemplary method. In this example, a tendon (supraspinatus M.) is being secured in place by a suture net 51 passing through a transosseus channel formed through the humeral head. The structure of the suture net 51 allows the surgeon to pull the suture net 51 through the channel from the lower portion of the channel to the upper portion of the channel. Then, the suture needles 81 may be used to draw the sutures 47 through the tendon and through a retention mechanism, such as the tabs 70 located in the retention end 11 of the suture net 51, for example. In this example, balls 43 assist the surgeon to adjust the tension on the sutures in discreet increments by pulling the balls 43 through holes in the tabs 70. Surprisingly, one or more of these devices provides for rapid attachment and adjustment of the fixation devices and substantially prevent suture pull through, which can lead to normal sutures working or cutting their way through the a portion of the bone that defines the transosseus channel.

Figure 10:
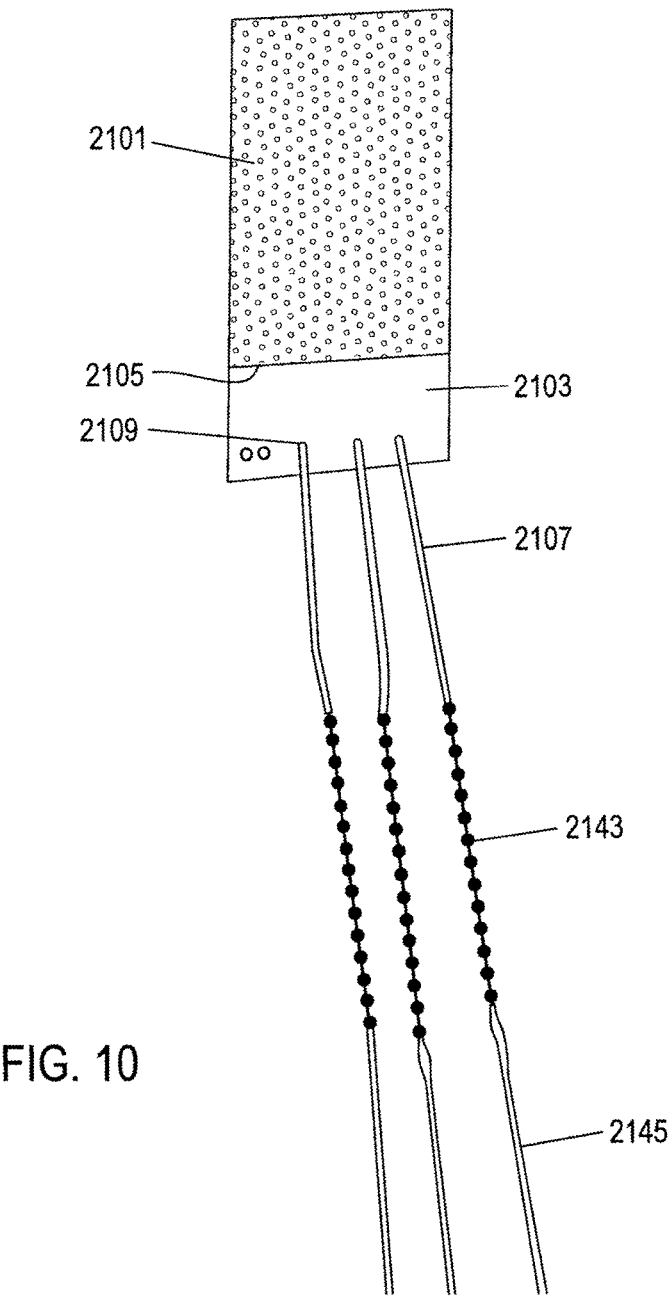
FIG. 10 illustrates one example of a mesh having a reinforced region to which one or more sutures may be attached by a user or may be pre-attached.

FIG. 10 illustrates a mesh 2101 having one or more sutures 2107 attached to a reinforced portion 2103 at an anchor point 2109. Each of the sutures 2107 may include a portion comprising raised portions 2143, such as beads, balls or the like. A lead 2145 may extend from the portion comprising raised portions. For example, the mesh may comprise a tape that includes one end 2103 that may be folded-over and joined together, such as by fusing, welding, stitching or the like. For example, the material may be a heat-processable material that can be fused together by heating, such as with the application of pressure during the heating process or, alternatively, without the application of such pressure. For example, the mesh may be made of a polyester, ultrahigh molecular weight polyethylene or the like. Herein, ultrahigh molecular weight is defined as a molecular weight greater than 300,000. In one example, the ultrahigh molecular weight polyethylene is covalently cross-linked. The additional stiffness and strength may provide a material that requires no tabs for retaining devices 2043, such as beads, balls or ratchet surfaces, formed or added to the ends of the sutures for temporarily or permanently fixing the sutures to a mesh tape 2001, such as with crosslinking caused by a chemical reaction or radiation or without such crosslinking.

The sutures 2107 extending from a mesh may be made of the same material as the mesh or may be made of a different material and may be joined to the mesh by a surgeon or a technician or may be pre-affixed at one or more anchor points. In one example, an anchor point may comprise one or more holes formed in the reinforced end, allowing a suture to be tied to the reinforced region by knotting one end of a suture through one or more of the holes. Beads, balls, ratchet surfaces and the like may be made integrally with the sutures or may be added, such as by fusing these features onto a length of suture, for example. Welding, bonding, adhering or press fitting may be used to add these retention or ratchet structures to the line of a suture, for example.

Figure 11B:
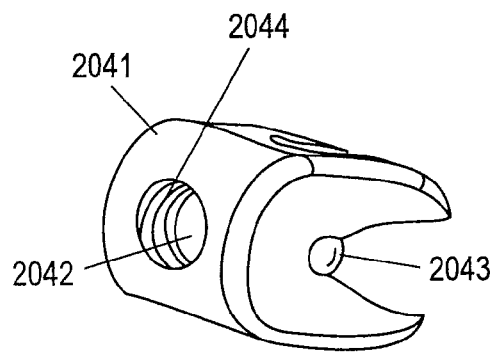
FIGS. 11A-C illustrate views of an example of a suture clip engaged on a raised portion of a suture with FIG. 11C illustrating how such a suture clip may be used with a mesh or net.
Figure 12A:
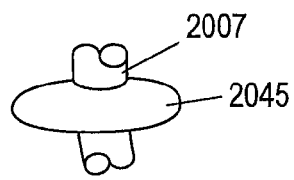
FIGS. 12A-B illustrate alternative forms for raised portions on a suture.
Figure 12B:
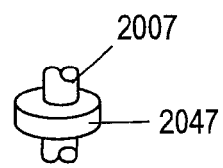
Figure 11A:
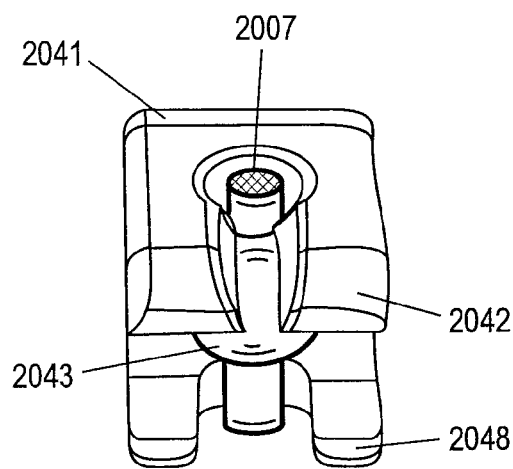
Figure 11C:
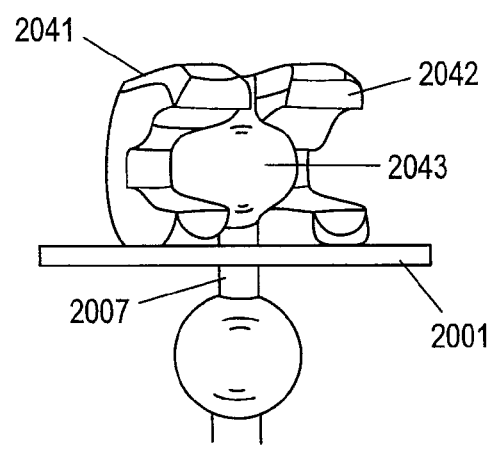
Figure 13:
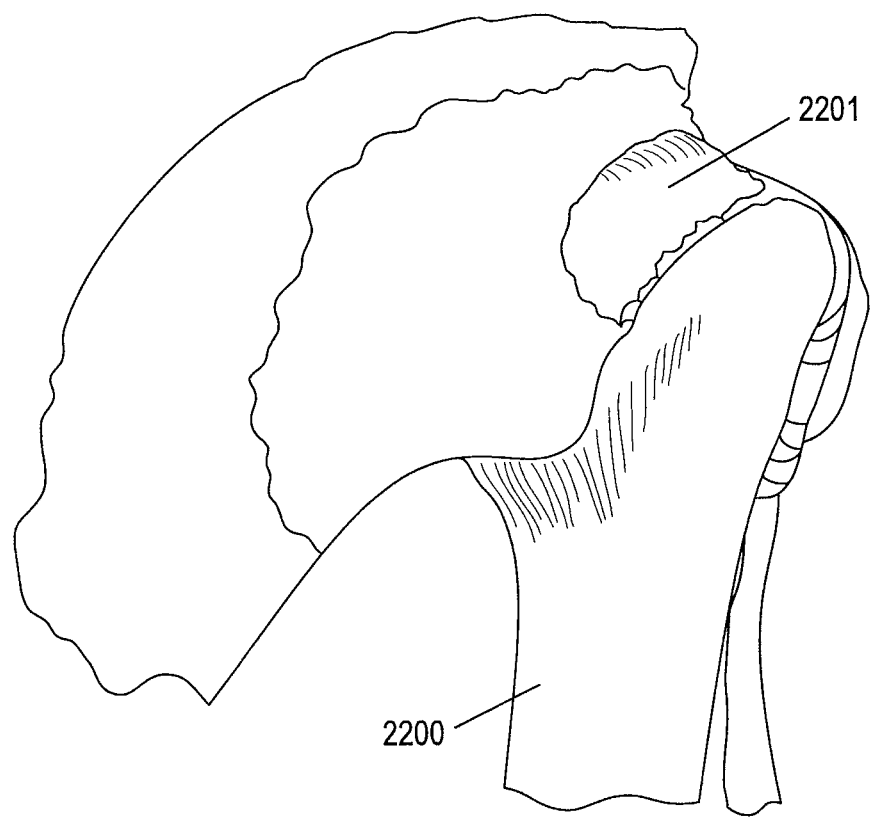
FIG. 13 illustrates a portion of a humerus bone that displays a torn tendon, as an example of a repair that may be benefited using a process including a mesh or net according to the examples.
Figure 14:
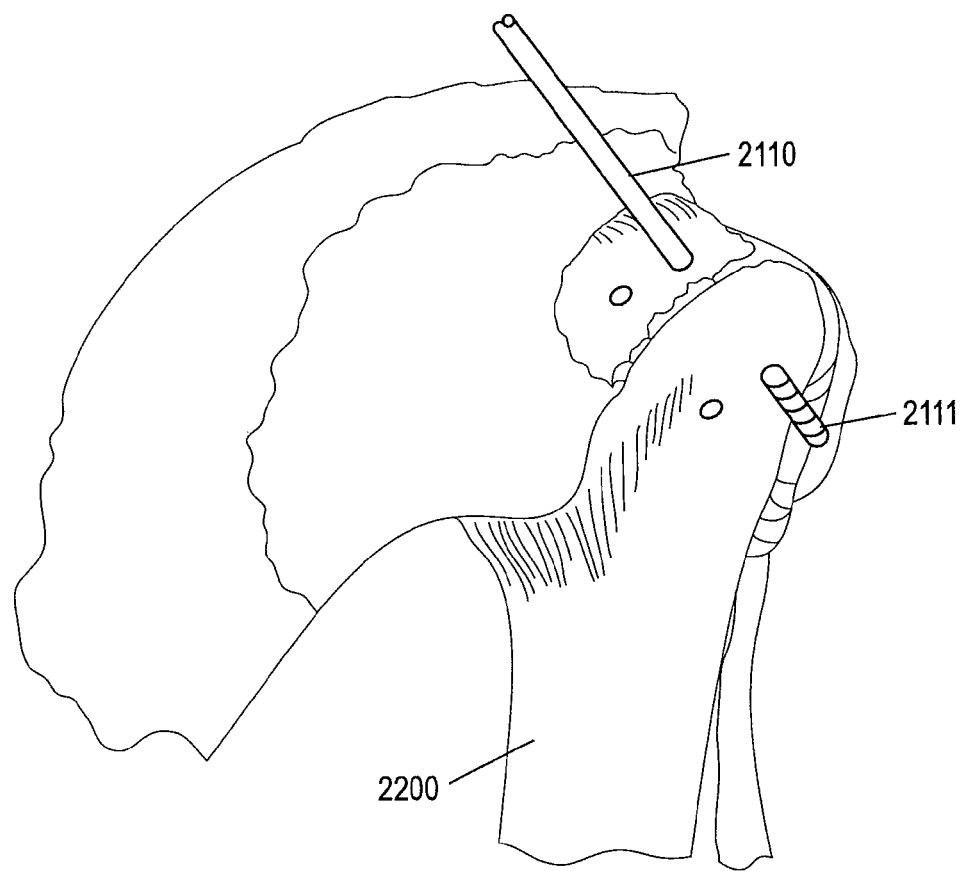
FIG. 14 illustrates a step in an exemplary process.

In one example, a clip 2041, such as illustrated in FIGS. 11A-C, may be added to aid in retention of a retaining device 2043, such as illustrated in FIGS. 10, 12A and 1B, for example. A tape 2101 may be disposed during surgery between a rotator cuff tendon and the skin, as illustrated in the process shown in FIGS. 14-18, for example. Sutures 2107 may be joined at one end to an end 2103 of the mesh tape and at an opposite end of the sutures 2107 to a different location of the mesh after passing the sutures through a bone anchor and/or the patients tissues, such as a bone tunnel, muscle and tendons, for example. A clip 2041 may be disposed between a mesh 2001 and the skin, as illustrated in the detailed view of FIG. 11C, for example. A low-profile clip may be used for a retaining device 2043 that is reduced in diameter or shaped as an oblate sphere 2045, disk 2047 or the like, as illustrated in FIGS. 12A-B, for example. In FIGS. 11A-C, a clip 2041 engages a retention portion 2043 of a suture, which retention portion 2043 is inserted into a conformingly-shaped recess of the clip 2041 defined by a plurality of prongs 2042. A tapered portion 2048 of each prong 2042 of a clip 2041 helps to spread the prongs as a force is applied to insert a spherically-shaped retaining device within the clip.

Figure 18:
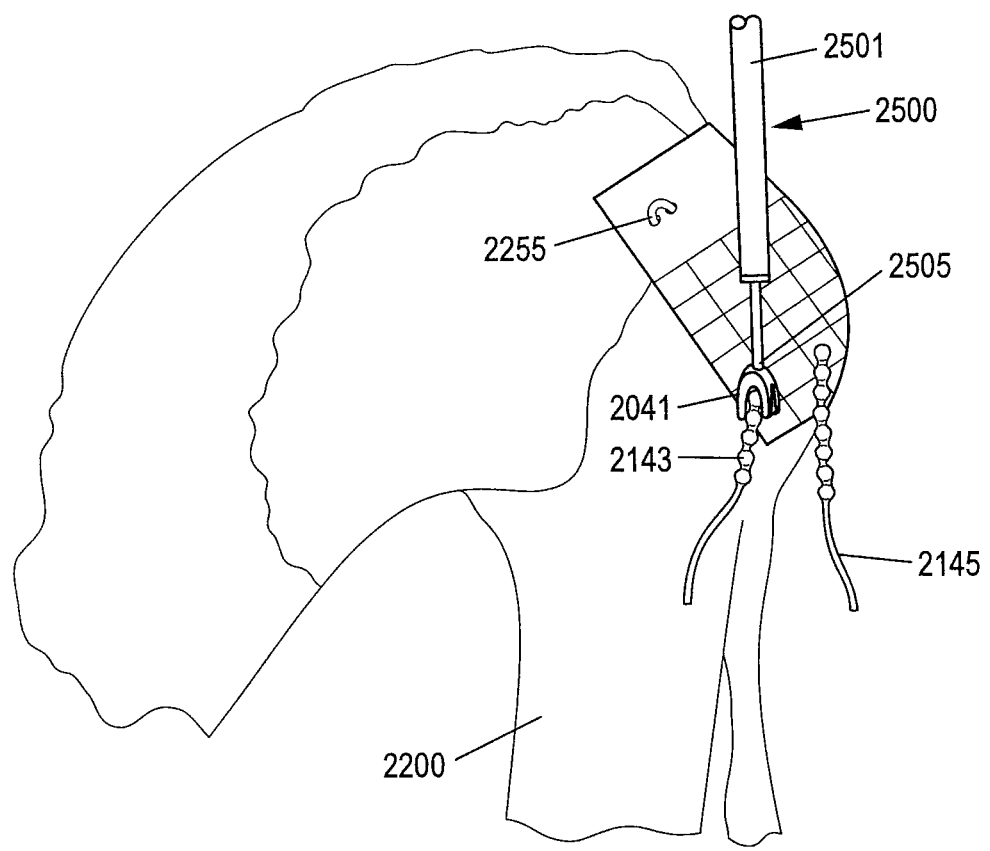
FIG. 18 illustrates a process for engaging a retention clip on a raised portion of a suture attached at one end to a reinforced portion of a mesh and on an opposite end by the raised portions extending through and engaging the mesh.
Figure 19A:
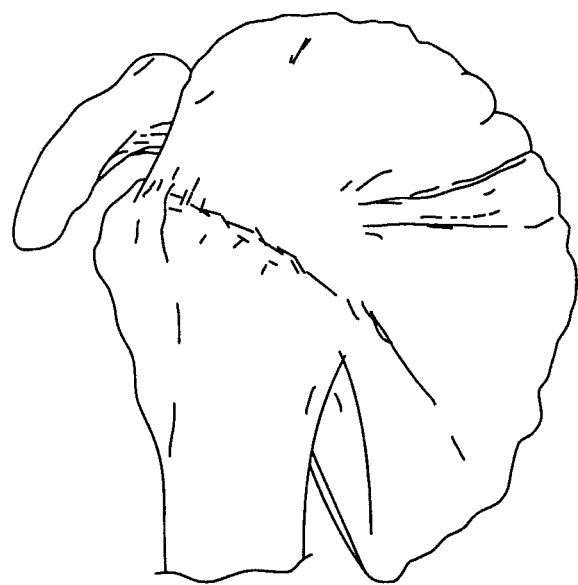
FIGS. 19A-B illustrate a humeral bone before and after a tear of a ligament.
Figure 19B:
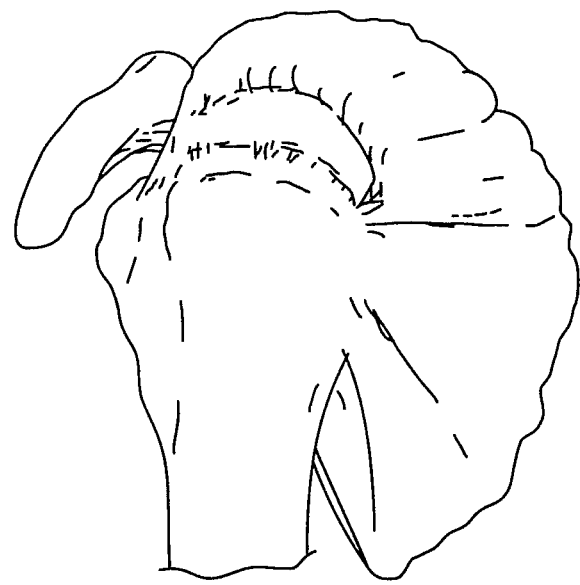

In the example of FIG. 18, a tool 2500 includes a handle 2501 removably attachable at one end 2505 to a hole 2042. For example, the hole 2042 may comprise threads 2044, and the tool 2500 may be threadingly engaged to the clip 2041. While the retention portion of the suture may be inserted through a tension by pressure of a stiff end of the suture or using a needle, a punch or the like to provide a hole in the tendon through which the retention portion is passed, reversibly or irreversibly, depending on the shape of the retention portion. For example, the retention portion may adjustably retain the suture in the tendon, allowing the user to apply a desired tension on the mesh or net. A clip may prevent the raised retention portion from being pulled back through the mesh, tape, net and/or tendon, as illustrated in FIGS. 11C and 18, for example. For example, using the tool 2500 in a minimally invasive procedure, the clip may be engaged onto the retention portion, when the retention portion is properly tensioned, and the tool may be withdrawn by unthreading the tool from the threaded hole in the clip.

The process for using a tape 2101 may be combined with a suture mesh 61 used as an anchor or with other anchors. If used with a suture mesh 61, the sutures of the suture mesh 61 may be inserted through the patient's tissue and through the tape 2101 to secure the patient's tissue between the bone and the tape 2101, for example. In the alternative or in addition to suture mesh 61 anchors, other bone anchors may be used or sutures with balls, beads or ratchet surfaces may be inserted directly through transosseous channels. Surprisingly, the balls, beads or ratchet surfaces may be capable of reducing or preventing undesired pull through (i.e. cutting through) of the suture in the transosseus channel, if the balls, beads or ratchet surfaced retaining devices extend along the portion of the suture that extends through the transosseus channel, allowing the surgeon to pass a suture 2107 through the channel without use of a suture mesh 61, for example.

The mesh, sutures and/or clips may be made of non-bioadsorbable materials such as a polyester, ultrahigh molecular weight polyethylene or the like or a bioabsorbable material, such as a polylactide (i.e. polylactic acid based polymers), polyglycolide (i.e. polyglycolic acid based polymers) or other biocompatible and absorbable polymers that break down and are absorbed over time (or combinations of these). In one example, glycolide-based copolyesters have aliphatic polyester based co-monomers or non-aliphatic polyester based co-monomers. For example, linear aliphatic polyesters, such as lactices, carbonates and epsilon caprolactones may be used or poly-p-dioxanone may be used with or without copolymerized radiostabilizers. In one example, a trimethylene carbonate or a may be used. A gamma sterilizable biocompatible and absorbable polymer may be used, such as a poly(ethylene 1,4-phenylene-bis-oxyacetate). Polylactides, such as poly-L-lactide (PLLA) may be used with or without copolymerization with aliphatic polycarbonates such as trimethylene carbonate and with or without the presence of self-eluting agents such as to manage local pH during degradation, reduce inflammatory responses or to prevent infections, for example. Polymers including a cyclic diester or poly(ethylene oxide) may be used in order to modulate hydrophilicity, for example. A poly(ester-amide) may be selected with film forming properties to form a mesh tape, for example, which may be degraded by enzyme and or nonenzymatic mechanisms. In one example, the material is a biologic, such as a poly-4-hydroxybutyrate, i.e. is biologically-derived or harvested from bacteriological or plant processes.

Figure 15:
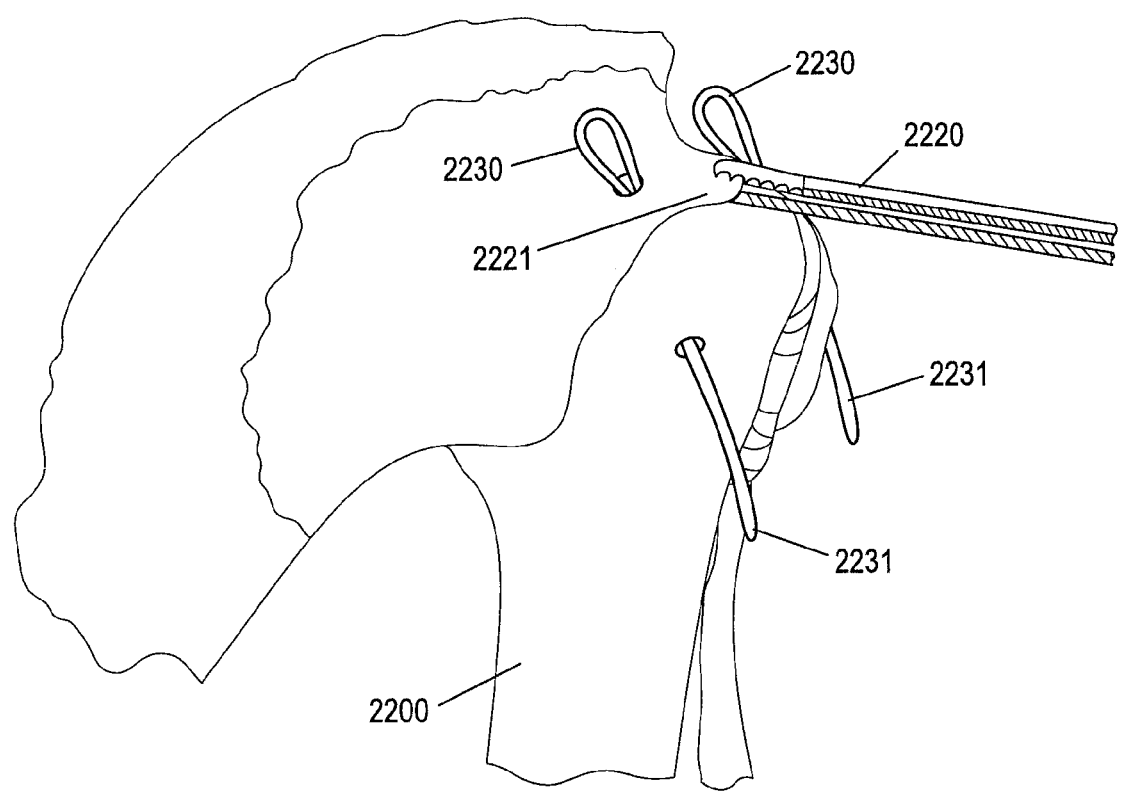
FIG. 15 illustrates a subsequent step in the exemplary process.
Figure 16:
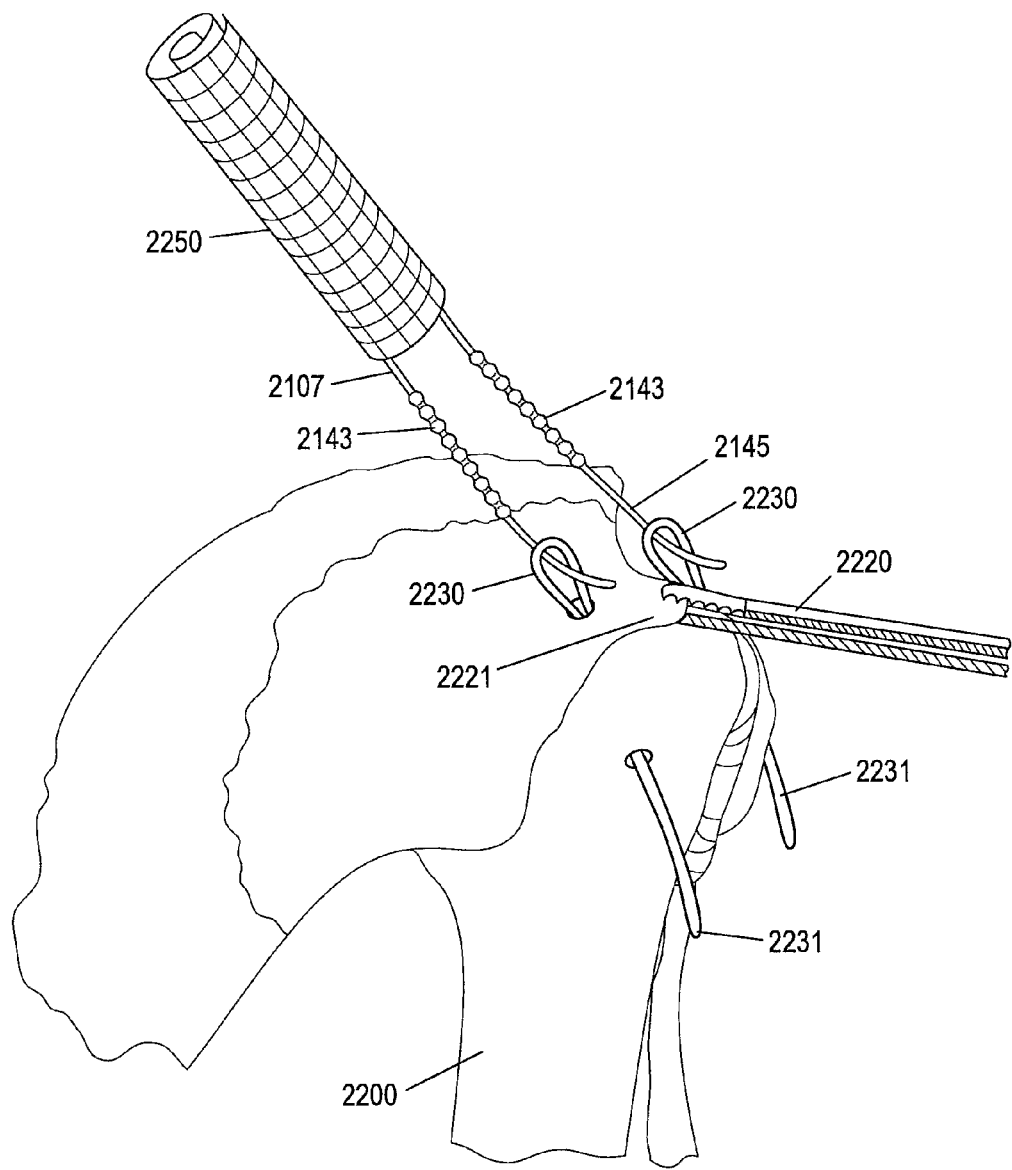
FIG. 16 illustrates another subsequent step in the exemplary process.
Figure 17:
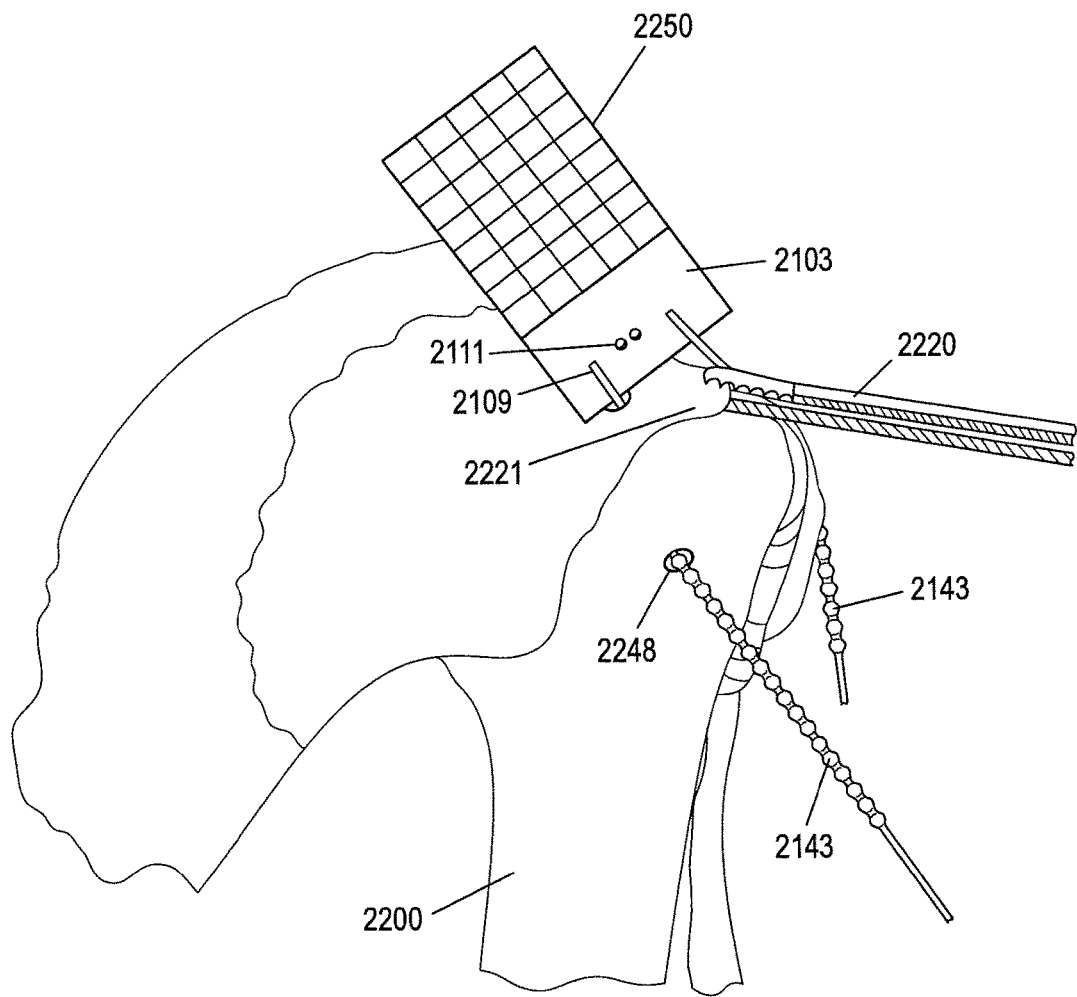
FIG. 17 illustrates yet another subsequent step in the exemplary process.

In FIGS. 14-18, an example of a process for using a mesh, such as a tape, is illustrated. A boring device 2110, such as drill, bores a hole through a bone, which may be bored as illustrated or may be bored in the opposite direction. In one example, a curved channel is bored to provide an arcuate transosseous tunnel. The end of the boring device or another device may be used to draw a snare 2230 through the tunnel formed in the bone, and the snare may be inserted through a hole formed in a tendon, as illustrated in the example of FIG. 15, for example, while a gripping device 2220 pulls a portion of the tendon 2221 into position on the humerus 2200. An opposite end 2231 of the snare 2230 extends out of the opposite side of the tunnel in the bone, allowing the surgeon to draw an end 2145 of one or more sutures through the tunnel in the bone using the snare 2230, as illustrated in FIGS. 16 and 17, for example. In FIG. 16, the mesh, net or tape 2250 is rolled in order for it to fit through a trochar, endoscope or other device being used in a minimally invasive procedure. In FIG. 17, the mesh, net or tape 2250 is unrolled and is pulled into position by the snares. A suture is anchored to the mesh at one end 2109. In FIG. 18, the mesh, net or tape is shown conformingly fit over a portion of the tendon and a portion of the bone, with an anchor point 2255 anchoring the suture on one end to the mesh, net or tape such as by forming a knot or stitch and at the other end the raised retention portion of the suture and the clip retain the mesh, net or tape in position and adjustably apply a tension on the mesh, net or tape. in one alternative, as illustrated in FIG. 17, holes 2111 may be provided as an anchor point for one or more sutures to be anchored to the mesh, net or tape. A tension may be applied up to one-half of the mean or median tensile force applied to the repaired tendon under normal conditions, for example. By retaining the mesh, net or tape in place by one or more sutures in this manner, the suture mesh, net or tape may secure the tendon to the bone without removing all of the load on the tendon. A tension may be selected by the surgeon for optimal healing of the tendon repair, for example.

Figure 20:
FIG. 20 illustrates the use of sutures in the prior art to repair a tendon with bone anchors inserted into a surface of the humeral head.
Figure 21:
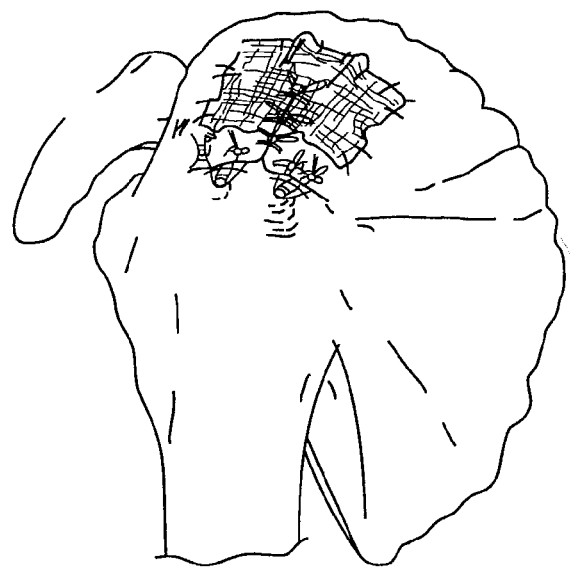
FIG. 21 illustrates a subsequent step for applying a net to reinforce the tendon using sutures to reinforce a tear in the tendon illustrated in FIG. 20.

Unlike the prior art, the suture net, mesh or tape may be used without bone anchors, the net, mesh or tape may extend over a portion of the tendon and over a portion of the bone where the particular tendon does not extend. Furthermore, the mesh, net or tape may distribute the load on the tendon over a larger surface of the tendon, as illustrated in FIG. 18 than would be the case for discrete suture knots and bone anchors as illustrated in the prior art drawing of FIG. 20, for example. Thus, the examples illustrate advantages over the prior art devices that fail to stimulate optimal healing and require greater time to complete a repair and potentially cause more damage to the repaired tendon.

What is claimed is:

1. A medical device for use in a surgical procedure, the medical device comprising:
   a mesh or net having a two-dimensional grid having a plurality of openings of predetermined size and shape;
   a retaining device; and
   a suture having one end affixed to the net or mesh, an opposite free end, and a plurality of raised portions positioned between each of the ends, the plurality of raised portions having predetermined size and shape adapted to be received through one of the plurality of openings in the grid of the mesh or net and adapted to directly engage the mesh or net to adjustably retain the one of the plurality of raised portions in position, so that the suture is retained adjustably in relation to the mesh or net, and
   wherein the retaining device includes a cavity within the retaining device, and the cavity engages the one of the plurality of raised portions of the suture adjustably retaining the one of the plurality of raised portions of the suture within the cavity of the retaining device when the suture is used during a surgical procedure with the mesh or net.

2. The device of claim 1, wherein the retaining device is a clip, and the one of the plurality of raised portions is retained by the clip.

3. The device of claim 2, wherein the clip has an upper portion defining a first slot joined to a lower portion defining a second slot and one of the plurality of raised portions of the suture is capable of being retained between the upper portion and the lower portion and the suture fits into the first slot or the second slot when the one of the plurality of raised portions is releasably retained between the upper portion and the lower portion of the clip.

4. The device of claim 3, wherein the upper portion is integrally formed with the lower portion of the clip.

5. The device of claim 2, wherein the clip includes four prongs extending in the same direction from a connecting portion joining each of the four prongs one to the other.

6. The device of claim 1, wherein the retaining device is a tab, and the tab is joined to the mesh or net.

7. The device of claim 6, wherein the tab is integrally formed with the mesh or net.

8. The device of claim 1, wherein the mesh or net is a cylindrical mesh or net.

9. A method of using the device of claim 1, comprising passing at least one of the plurality of raised portions of the suture through the openings of the mesh or net during suturing, as the suture is pulled through the mesh or net, and retaining one of the plurality of raised portions from passing back through the holes, such that the raised portion of the suture is retained by the mesh or net, at least temporarily, during a surgical procedure, unless the suture is cut and or an external force that exceeds the internal forces applied by patient physical exertion is applied by the surgeon to remove the suture.

10. The method of claim 9, further comprising:
    securing at least one of the plurality of raised portions using the retaining device, wherein the retaining device is selected to be a clip or a tab.

11. The method of claim 10, wherein the step of securing includes inserting the suture into a slot on the clip such that the at least one raised portion is fixed within the cavity of the retaining device between an upper portion of the clip and a lower portion of the clip.

* * * * *